United States Patent [19]
Hamilton et al.

[11] Patent Number: 6,070,264
[45] Date of Patent: Jun. 6, 2000

[54] WELDING HELMET HAVING AUTO-DARKENING AND MANUALLY ADJUSTABLE LENS SHADE CONTROL

[75] Inventors: Thomas J. Hamilton, Holland, Mich.; Steven F. Kickham, Wildwood, Mo.; Jerry Charles Cole, Pleasant Lake; David Allen Shamery, Hudsonville, both of Mich.

[73] Assignee: Jackson Products, Inc., Chesterfield, Mo.

[21] Appl. No.: 09/289,257

[22] Filed: Apr. 9, 1999

[51] Int. Cl.$^7$ ........................................................ A61F 9/06
[52] U.S. Cl. .......................................... 2/8; 2/906; 349/14
[58] Field of Search .................................... 2/8, 431, 432, 2/905, 906; 349/14, 13, 104; 359/246

[56] References Cited

U.S. PATENT DOCUMENTS

| | | | |
|---|---|---|---|
| 4,155,122 | 5/1979 | Budmiger | 2/8 |
| 4,863,244 | 9/1989 | Fuerthbauer et al. | 2/8 X |
| 5,377,032 | 12/1994 | Fergason et al. | 2/8 X |
| 5,751,258 | 5/1998 | Fergason et al. | 349/14 |

*Primary Examiner*—Peter Nerbun
*Attorney, Agent, or Firm*—Howell & Haferkamp, L.C.

[57] ABSTRACT

A welding helmet includes a shutter assembly with an electronically controlled liquid crystal shutter in a compact housing for physical mounting near the face area of a protective shell. The electronic controls provide for the customary auto-darkening function as well as two user selectable fixed shade settings which permit the user to fix the shutter shade in one of a plurality of preselected and factory set shade settings. When fixed at a shade setting, the user is given a visual indication that the helmet is not in an auto-darkening mode. The housing allows for two PC boards to be mounted above and below the optical shutter, with a flexible cable interconnecting the two PC boards so as to not interfere with or obscure the user's vision. The controls are all single function, readily accessible and continuous so that multiple operation of any one control does not switch the associated function off, allowing a user to continuously operate any control repeatedly to ensure its selection. As the electronics and shutter are self contained in a single housing, ready assembly and field change out are accommodated.

37 Claims, 8 Drawing Sheets

WELDING HELMET HAVING AUTO-DARKENING AND MANUALLY ADJUSTABLE LENS SHADE CONTROL

BACKGROUND OF THE INVENTION

Welding helmets are known in the art and generally include a protective shell head covering, a head strap for holding the shell in position on the head, and a lens through which the wearer views the work. One of the more useful and commercially successful improvements to the lens has been the prior development of an auto-darkening lens or shutter assembly. This feature provides a liquid crystal shutter and an electronic circuit for automatically sensing the presence of the welding arc and then darkening the liquid crystal shutter in response thereto so that the welder can keep his helmet in place and continue to have his face protected even while he is not welding, amongst other advantages. Even while in the clear state, the shutter protects the welder's eyes from harmful UV, flying debris, etc, and by providing a shutter that changes its light transmission qualities from dark to light these advantages may be realized.

Over the years, patents have been issued for improvements related to the liquid crystal lens, and the electronic circuitry used to drive the lens or shutter. Examples include U.S. Pat. Nos. 5,074,647; 5,347,383; 5,252,817; 5,248,880; 5,208,688; and others, the disclosures of which are incorporated by reference. This auto-darkening shutter assembly feature has been the focus of much inventive activity at least in part because of the perceived value to the user of keeping the helmet on the user's head and in the operable position to protect the user's eyes and face even if he is not welding. This provides a tremendous safety advantage and can significantly reduce the risk of injury to a skilled welder who would be difficult to replace.

In order to further improve the welding helmet and provide still another feature that will increase the number of work situations and hence the amount of time that a welder can keep his helmet on and in the operable position, and one which will provide the welder with even greater personal control over his helmet and shutter assembly, the inventors herein have succeeded in developing a manual control which permits the welder to fix the shutter shade level and disable the auto-darkening circuit at the same time. The invention allows for two, or more, preselected shutter shade levels to be conveniently chosen by the welder as the helmet remains in place and an indicator light inside the helmet which reminds him which mode he has selected. When these fixed shutter shade levels have been chosen by a manual control, the control does not allow the shutter to convert automatically into the auto-darkening mode. In other words, upon manually selecting a fixed shade setting, the welder has fixed the shade setting until he manually changes the control back into the auto-darkening mode, or for that matter into another fixed shade setting. The shades preferably considered by the inventors to be most useful to a welder are clear (a nominal shade 3 due to the limits of the liquid crystal shutter) and a mid-level shade 5, as said shade levels are known in the art.

The clear shade is chosen to allow the welder to have a relatively clear view through the shutter so that he can get his work ready, and perform any other work related tasks without any substantial impairment of his vision. A shade 5 setting allows a welder to perform certain types of welding which do not generate the extremely bright light of electric resistance welding, such as torch welding as is commonly used in muffler shops, etc. With these kind of welding operations, the welder would ordinarily take his helmet off and switch to goggles or another helmet having a fixed shade 5 lens. This is undesirable as it requires additional equipment, takes time, etc.

The controls preferably used to permit the welder to select these fixed shade settings are a plurality of pushbuttons mounted directly on the same enclosure which houses the shutter, other commonly provided controls and the electronic control circuit contained on one or more circuit boards. Indeed, another aspect to the present invention is the novel arrangement of the pushbutton controls inside the helmet and at the lower end of the control housing so that the welder may conveniently reach up inside the helmet as it remains in an operable and protective position and change the shutter shade setting. The control housing also has a visual indicator which preferably is a two color LED which illuminates amber or green to indicate to the welder that he has manually selected a fixed shade of shutter level illuminates amber or green to indicate to the welder that he has manually selected a fixed shade shutter level. This serves as a constant reminder so that he does not mistakenly take up his welding and expect the shutter to auto-darken. As a further safety feature, the visual indicator preferably goes dark when the auto-darkening mode is selected so that the welder need only be sensitized to whether any light is on to remind him not to expect auto-darkening. In other words, as a reflex the welder need only keep in mind that any visual cue of the illuminated LED means no auto-darkening.

The pushbuttons are preferably provided with one for each fixed shade setting and another for auto-darkening. The control circuit is configured so that each pushbutton only selects that feature, and does not also turn that feature off. In other words, the welder can push the "clear" pushbutton any number of times and all he has done is select the clear shutter shade level. This allows a welder to push any button any number of times and be sure about the shutter shade setting without fear of shutting it off or shifting to any other shade setting. This can be important as welding can be a tough job in an unfriendly environment and the welder's hands likely have thick gloves on them so that as he reaches up into the helmet to make his control setting he should not be asked to make fine distinctions in operating the buttons.

Still another aspect to the present invention is the control housing and arrangement of the circuit boards within the housing and surrounding the shutter assembly. It is important for manufacturing and assembly that the shutter housing be separately made and then assembled to the protective shell. This reduces manufacturing costs and allows the various controls and electronics to be conveniently changed out in the field should the shutter assembly need replacing. This prevents the entire helmet from being discarded should only the electronics fail. However, implementation of the present invention requires additional electronics and it needs to be preferably located in the same housing. The dimensions of the helmet and especially the face and eye portion of the helmet limit the space available for locating these electronics as they are routinely mounted on a printed circuit (PC) board for high speed pre-assembly. However, the now standard controls and circuitry are routinely mounted above the shutter and consume virtually the entirety of that available space. The shutter is generally sized to fill virtually the entirety of the width of the available space near the eye so as to maximize the viewing area for the welder. This creates a problem for adding a PC board below the shutter as the electronics are most conveniently designed for interconnection with the "standard" controls for the auto-darkening feature. In order to solve these and other problems in the prior art, and to allow for the addition of another PC board beneath the shutter that can be interconnected with the existing PC board above the shutter all within a single housing, the inventors have succeeded in designing a housing that is extended in length and has made use of a strap like cable extending between the top PC board and the bottom PC board. The cabling preferably is minimized in size through the minimization of the number of wires needed to interconnect the two boards and is also preferably a flat strap that may be folded over and fit conveniently within the relatively narrow sides of the housing that border the shutter. In this way, the extended lower half of the housing may conveniently house the second PC board and the pushbuttons be mounted directly onto the second PC board, using techniques known in the art. Note that this arrangement also conveniently locates the pushbuttons near the bottom of the housing where they are most accessible for the welder to reach up into the mask and operate.

The electronic circuitry preferably used by the inventors is elegantly simple to minimize cost and the size of the PC board that mounts it. Several features are included in the circuitry which enhance the invention. These include the ability of the preselected shade level settings to be adjusted at the factory so that the manufacturer can conveniently offer a helmet offering a shade 5, or some other shade level as a fixed shade level. By using infinitely variable potentiometers, the shade level setting may be fine tuned to ensure compliance with industry standards regardless of variation in other electrical components. Other circuitry features will be explained in the preferred embodiment.

While the principal advantages and features have been briefly described, a greater understanding of the invention may be attained by referring to the drawings and the detailed description of the preferred embodiment which follows.

DETAILED DESCRIPTION OF THE PREFERRED EMBODIMENT

Figure 1:
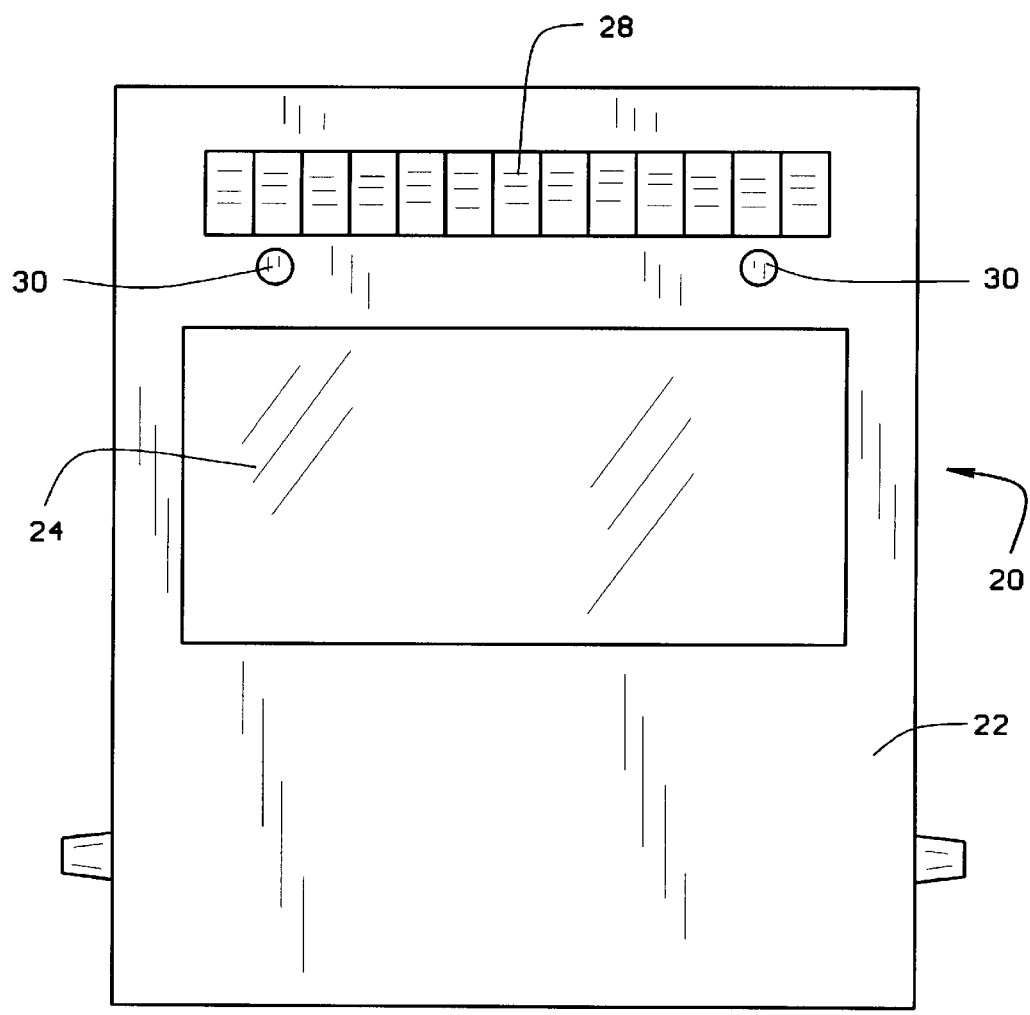
FIG. 1 is a front perspective view of the shutter assembly as ready for assembly into a protective shell to complete the helmet.
Figure 2:
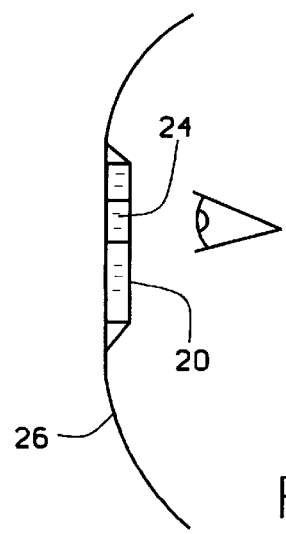
FIG. 2 is a side diagrammatic view of the shutter assembly mounted in a protective shell to form a helmet.

The present invention comprises a liquid crystal shutter assembly 20 as shown in FIG. 1 housed in what is preferably a high impact plastic clam shell case 22 with a liquid crystal shutter 24 providing a lens through which a welder views his work as the helmet 26 is worn, as is shown in FIG. 2. It can be appreciated that FIG. 2 is not drawn to scale and is merely provided to depict the various elements of the invention and how they are arranged. Referring back to FIG. 1, also shown is a solar cell 28 for generating electricity to operate the electronics and help extend the operating life of the battery, as explained below. One or more photosensitive transistors 30 are also mounted in the outside surface of the housing or case 22 to detect the bright light emanating from the welding operation and trigger the electronics, again as is explained in greater detail below.

Figure 3:
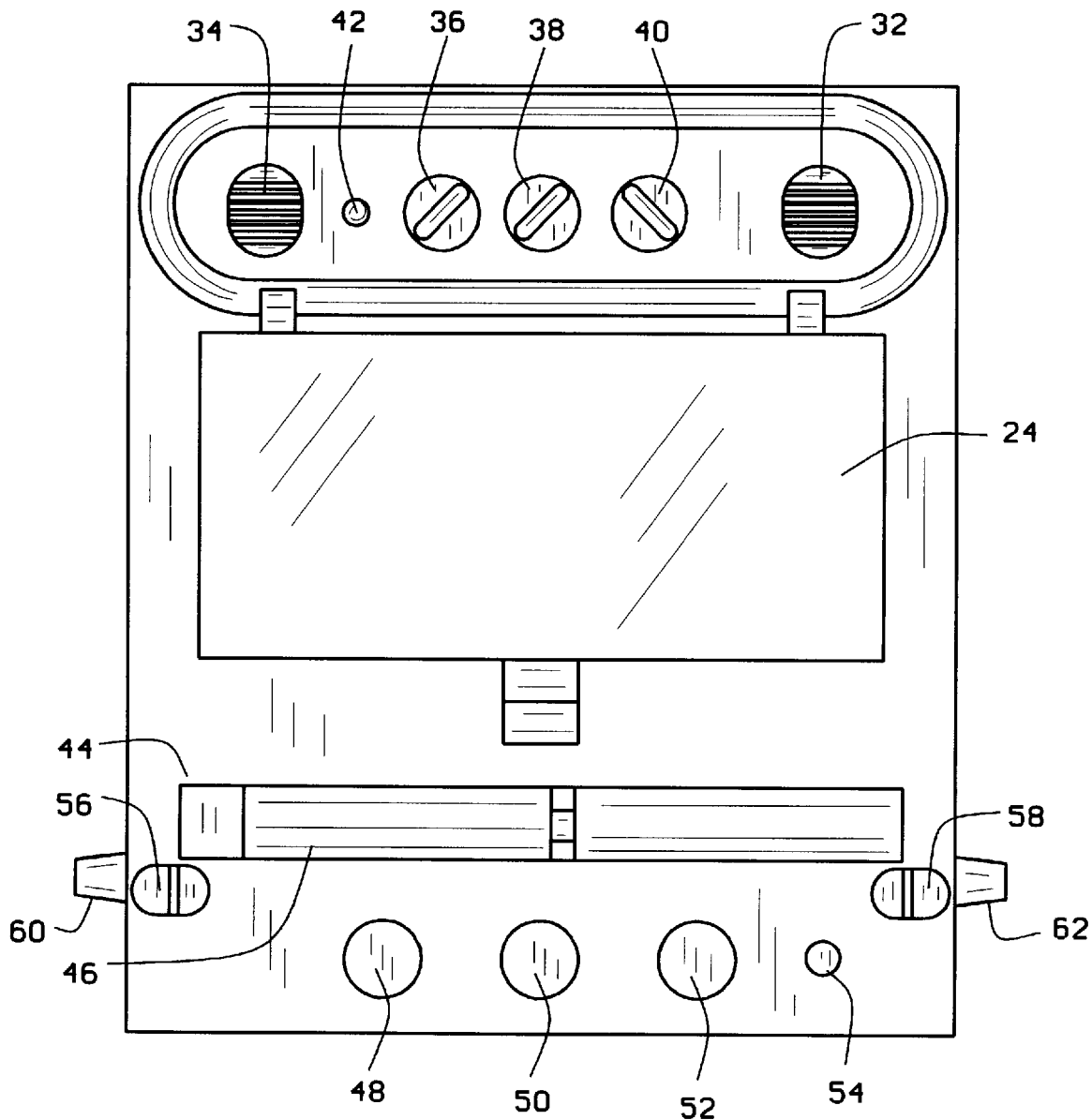
FIG. 3 is a rear perspective view of the same shutter assembly as depicted in FIG. 1 detailing the various controls as would be facing the welder inside the helmet as it is worn.

The opposite side of the housing 22 is shown in FIG. 3 and depicts the surface which is exposed to the welder's face as the helmet is worn. Again one sees the shutter 24 through which the welder views as the helmet is worn. Across the top of the housing are the controls provided for the auto-darkening circuitry. At either side are the on button 32 and the off button 34 and they flank the three selector switches "shade" 36, "sensitivity" 38, and "delay" 40, the operation of which will be explained below. Lastly, there is a low battery light 42, which is preferably a red LED. At the bottom of the housing 22, and below the shutter 24, are the additional controls providing for fixed shade operation. A battery compartment 44 provides the physical mounting location for one or more batteries 46. Below the battery compartment 44 are three pushbuttons. From left to right they are the fixed shade one button 48, the weld button 50, and the fixed shade two button 52, the operation of which will be explained below. At the far right is a visual indicator 54 which is preferably a two color LED which indicates that the welder has selected either fixed shade one, fixed shade two, or weld, all of which will be explained below. There are also two finger slide buttons 56,58 for retracting a pair of spring loaded tabs 60,62 for insertion of the shutter assembly into a receptacle (not shown) in the helmet and which along with grooves (see FIG. 4) serve to mount and mechanically interlock the shutter assembly into the helmet.

Figure 4:
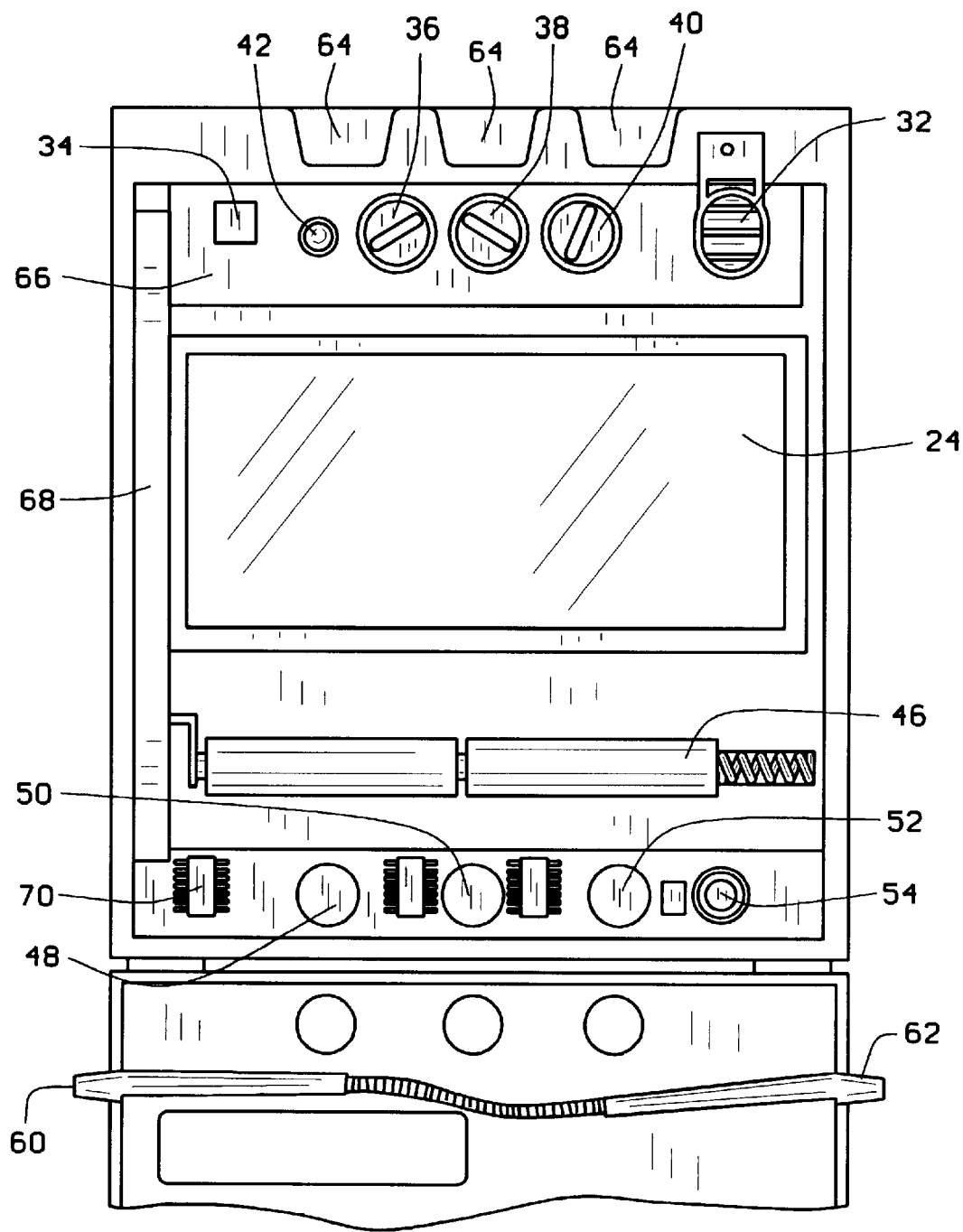
FIG. 4 is a view of a partially disassembled shutter assembly exposing the two PC boards and other internals of the shutter housing.

Referring now to FIG. 4, the housing has been opened up to expose the inside configuration and mounting of the various components of the shutter assembly. Three grooves 64 near the top of the case 22 fit into complementary lugs (not shown) in the shell 26 to help secure the shutter assembly 20 in place. Perhaps more importantly, the top circuit board 66 is shown mounted above the shutter 24, with a flexible strap like cable 68 interconnecting it to the bottom circuit board 70 mounted below the shutter 24. A bottom hinged portion of the housing 22 is shown folded down to expose the battery compartment 44 and the spring loaded tabs 60,62.

Before the details of the electronics are explained, a brief overview will perhaps be helpful of the functional operation of the present invention, which combines an auto-darkening welding shutter with a plurality of fixed shade level settings into a single unit and a visual indicator of the selected setting. The auto-darkening or weld function acts as a light shutter, controlling the light transmission without distorting, or at least with relatively minimal distortion of the light and the image characteristics carried by the light or represented by the light. Simply stated, the unit turns the light shutter from a near clear to a dark shade. The unit senses the light from a weld and controls the transmission of electromagnetic energy, such as light in the visible, infrared and/or ultraviolet wavelength ranges. As in existing welding helmets, the shutter may have one or more operational characteristics that the user may control, such as shade, sensitivity, and delay. The shade adjustment varies the amount of light that is transmitted through the shutter when the unit is in the light blocking or welding mode. The amount of light transmittance is referred to as the shade. The delay control adjusts the time during which the shutter remains in the dark state after a condition calling for the dark state ceases, such as an interruption or termination in the bright light during welding. The third control mentioned herein as typically found is the sensitivity adjustment which changes the sensitivity to the detection of light. This affects the distinction between ambient conditions and the bright light condition occurring during a welding operation. These controls and adjustments are provided for the welder's viewing comfort. During the weld mode the associated indicator light remains off, as the welders eyes are protected should a welding operation begin. Further, with the circuitry disclosed herein, the weld mode is the default mode as power is supplied to the unit, either initially or when the power is turned on. Pushbutton 50 may also be used to select the weld mode.

A second mode, providing a fixed shade mode, is referred to as a grind mode (nearly clear). This mode is selected by pressing pushbutton 48. When this mode is selected, and the third mode as well, the auto-darkening mode is disabled and the shutter is "locked" into a fixed shade setting. This fixed mode setting is useful for operations when the unit is exposed to bright light but the welder does not want the shutter to go dark. Examples include grinding burrs from welded pieces of metal, walking around in a well lighted area, etc. This mode enables a welder to see without changing the other "weld model" settings, described above. A visual indicator is illuminated to indicate to a welder that he is not in the weld mode so that he will remember to switch to weld mode before he begins welding. In the preferred embodiment it includes a bi-color LED which lights as green.

A third mode, providing a fixed shade mode, is referred to as a torch mode (fixed shade 5). This mode is selected by pressing pushbutton 52. During this mode the shutter is set and kept at a fixed shade 5. The particular shade level can be preselected at the factory and may be any shade, although shade 5 has been chosen by the inventors as preferable for their preferred embodiment. This mode allows a welder to select a lighter fixed shade setting than the shade adjustment mentioned above and without changing the "shade" control setting used during the normal weld mode. A shade 5 setting has been particularly selected as it is considered as appropriate for torch welding, for which the welder would have to otherwise remove his helmet and put on welders goggles or another helmet with a fixed shade plate (instead of a shutter). Again, a visual indicator is given to the welder in the form of the same bi-color LED that lights amber.

The present invention may be used in the welding helmet disclosed in this preferred embodiment, or in a face mask or other type of device that would be used to protect the face or eyes of a person in the field of welding, grinding, or other industrial or manufacturing activity.

Figure 5:
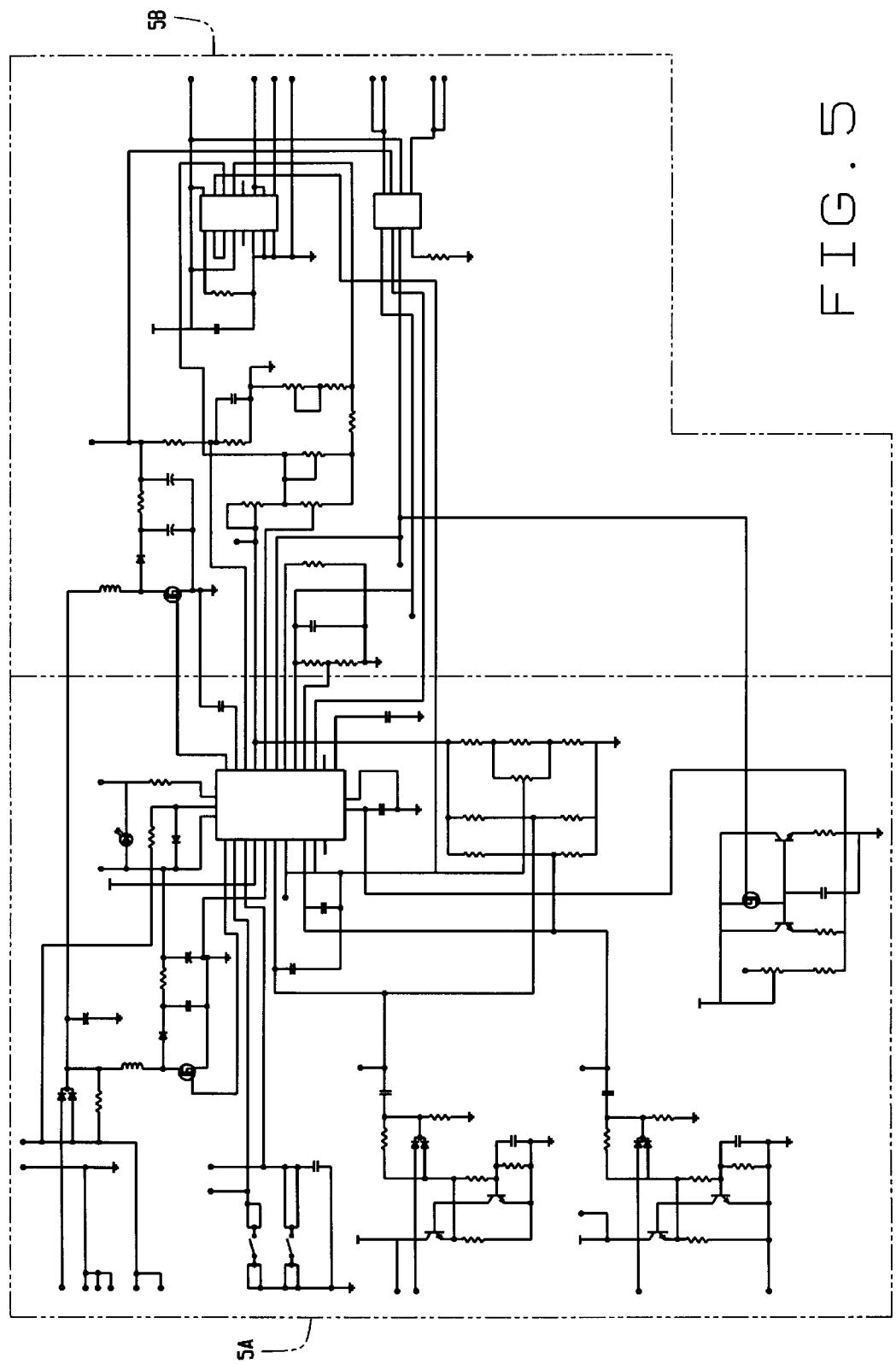
FIG. 5 is a schematic diagram of the electronics comprising the top PC board having the "standard" auto-darkening controls.
Figure 5A:
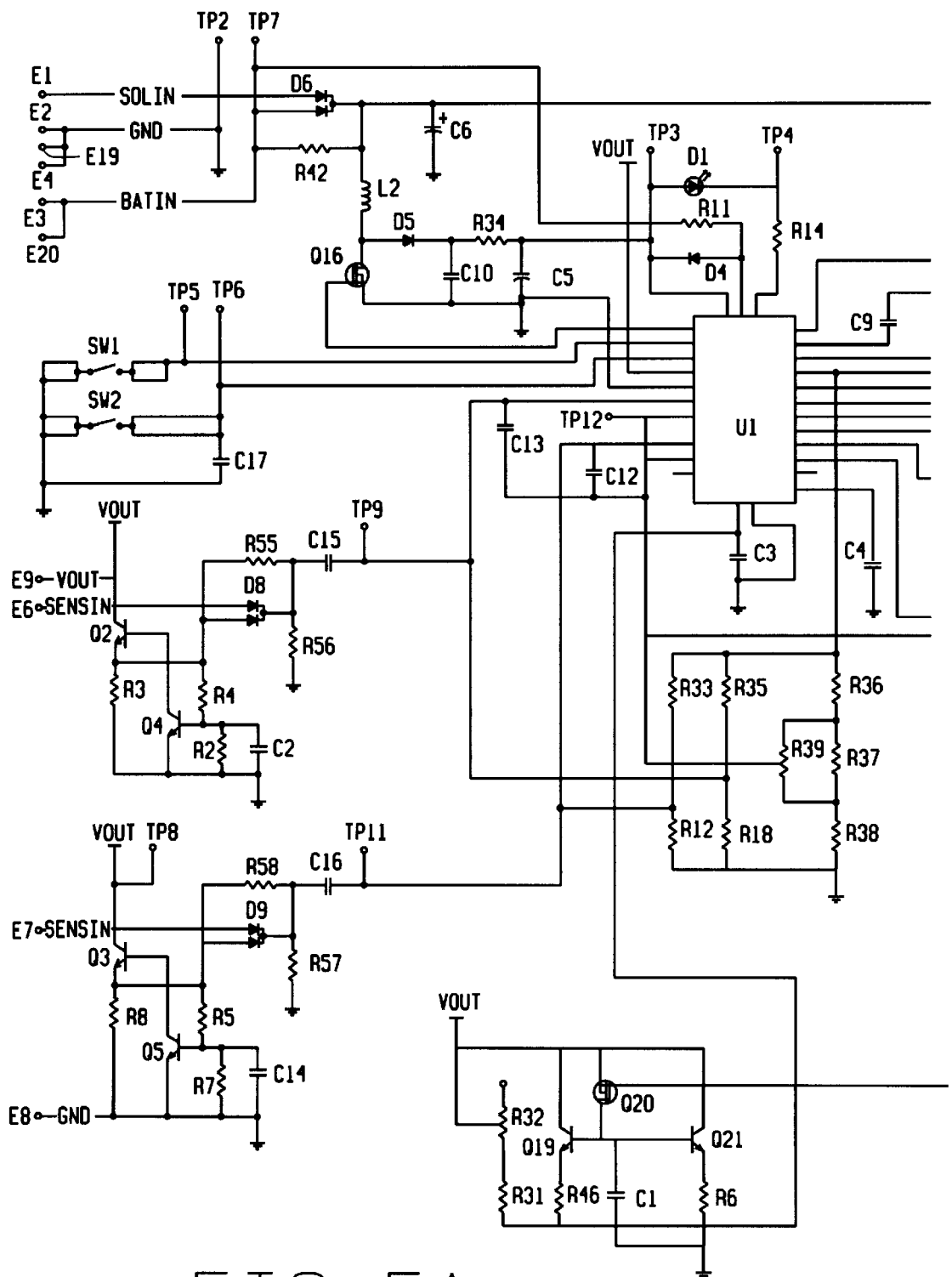
Figure 5B:
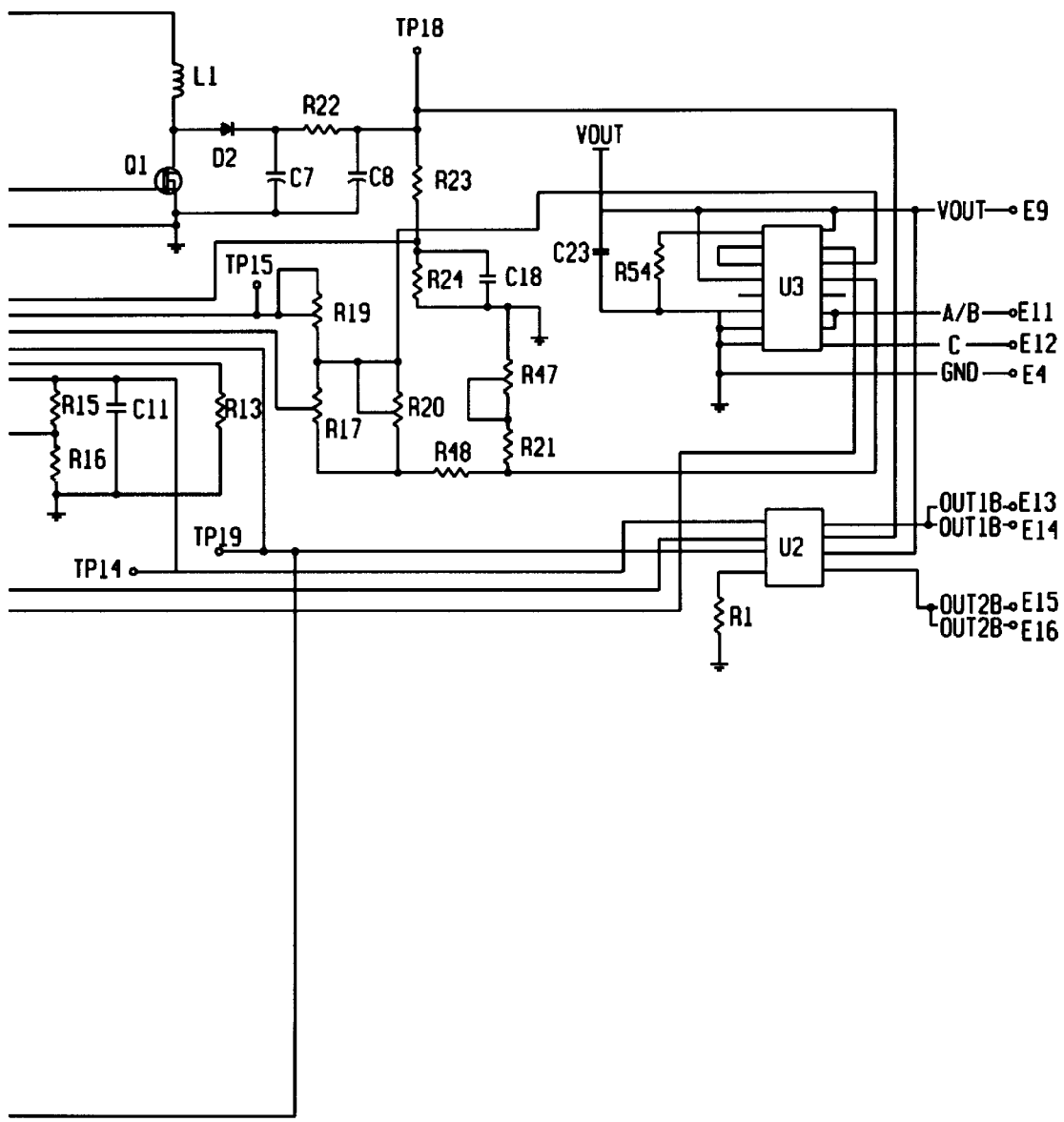

Turning now to the detailed electronic circuitry, reference is made to FIG. 5. As shown therein, power is applied by pushing SW1 and turned off by pushing SW2. Note that the welder can not mistakenly turn off the power by pushing any button twice or any number of times. He must affirmatively select the off button SW2. These two inputs are monitored by U1, an ASIC in the preferred embodiment but which could be any logical device such as programmed microprocessor. When turned on, U1 then starts increasing the 3 volts supplied by the batteries at "batin" and assisted by the voltage supplied from the solar cell 28 at "solin" to a 5.8 volt level. This is achieved through a buck/boost circuit, as known in the art. One side of L2 is at 3 volts and the other side is periodically grounded by a FET Q16. This creates current through L2 during the pulse and L2 will try to maintain this current by increasing its voltage. The increased voltage then flows through D5 and the voltage pulses are then filtered through C10, R34 and C5 and sent to U1 pin 2 as 5.8 volts (VCC). The filtered 5.8 volts is then monitored by U1. If the voltage drops below 5.8 volts, U1 will send another pulse signal to the FET Q16 causing the voltage to rise back to 5.8 volts. U1 will time out in approximately twenty minutes, if the on button SW1 is not pressed or if the unit does not respond to welding light. A battery low signal is provided by U1 if as it monitors the battery voltage at pin 2 it drops below 1.8 volts by causing the LED D1 to pulse through periodically grounding pin 21 (LEDOUT).

When the shutter is closed calling for a dark shade, the high voltage is generated similarly to that as described above using L1, FET Q1, D2, and filtering the voltage pulsed with C7, R22 and C8. The difference is in the sensing of the low voltage. This is determined by the difference in the voltage set by R23 and R24 (HVFB) and the voltage set at U1 pin 26 (HVSET). The high and low values are set during production using R19 and R20. These high and low values are set to limit the voltage to the shutter and provide a user window of shade adjustment that can be made with R17. When the unit is calling for the shutter to be open or clear, the HVFB is compared to 3.4 volts (internally in U1), creating approximately 40 volts across C8. This voltage is used to send 40 volts to the shutter for a short time when the unit calls for the shutter to go dark. This short 40 volt charge enables the shutter to close (go dark) faster. In other words, it provides a fast transition from clear to dark to minimize the transmission of harmful light energy through the shutter at the beginning of a weld.

Figure 6:
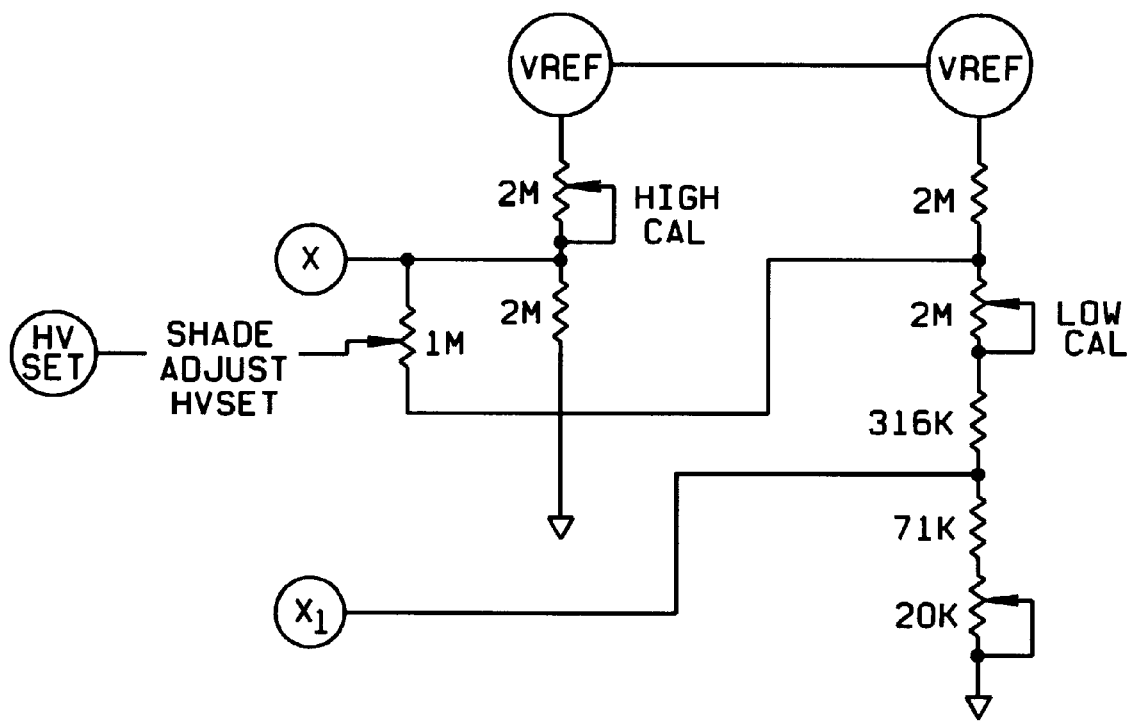
FIG. 6 is a schematic diagram of the electronics comprising a second possible shade adjustment circuit.

As shown in FIG. 6, an alternate circuit may be substituted for the high and low voltage set circuit shown in FIG. 5. This circuit may be connected between the circuit nodes labeled as X, X1, VREF, and ground. This alternate is thought to make the factory adjustment of the high and low voltages easier as it reduces any tendency for the two adjustments to interact.

When a welding operation is commenced, light is sensed at the phototransistors Q2 or Q3, allowing current to flow. Q4 and Q5 control the current through the phototransistors Q2 and Q3. An AC voltage is developed across R3 and R8 as sensed from the welding light, and passed through a high pass filter (R55, C15, C13 and R58, C16, and C12) to U1 pins 18 and 15 whose signal levels are set with R33, R12 and R35, R18. The sensor signal levels are then compared to the sensitivity levels user set at U1 pin 17 and 14 (THRES1 and 2) by R39. This THRES voltage is developed from VREF and set by R36, R37, R38 and R39. The users sensitivity setting/voltage R39 may be adjusted by the user at any time. If the sensor voltage level, U1 pins 18 and 15 (SENSE 1 and 2), becomes higher than the sensitivity threshold voltage level, U1 pins 17 and 14 (THRES 1 and 2), U1 will enable the high voltage to the filter by making HVEN high (U1 pin 22 and U2 pin 3), allowing U2 to send the high voltage coming in at U2 pin 7 to be placed across the filter U2 pins 5 and 8. The polarity is set by U2 pin 2 (POL) and alternates at a frequency set by U1 VOUTCAP (C4). The HVSET will allow the user to adjust the voltage between the high and low value at any time, allowing the shade achieved during the weld mode to be changed, by use of the shade knob R17. If the sensor voltage level drops lower than the sensitivity threshold voltage level, HVEN will go low, (a delay may be added by the users delay adjustment) and U2 will use (LVIN) a 4 volt DC voltage. U2 changes the 4 volts to a 3.5 volt square wave, (polarity is set by U2 pin 2 POL) to drive the filter, causing the filter to go clear. U1 pin 7 VREG, which supplies U2 with 4 volts, is monitored and regulated using R15, R16 and U1 at U1 pin 6 VRSET. R15 and R16 provide a voltage divider that is compared inside U1 to VREF (3.4 volts).

As noted above, an adjustable delay may be user added to delay the filter before going clear. The delay is set at U1 pin 20 using C3, R31, and a user adjustment R32 (DELAY knob). An optional fixed delay is also present on the board that uses Q19, Q20, Q21, R6, R46, and C1. When not used, R46 is simply removed or, if used, the delay knob is uninstalled.

Figure 7:
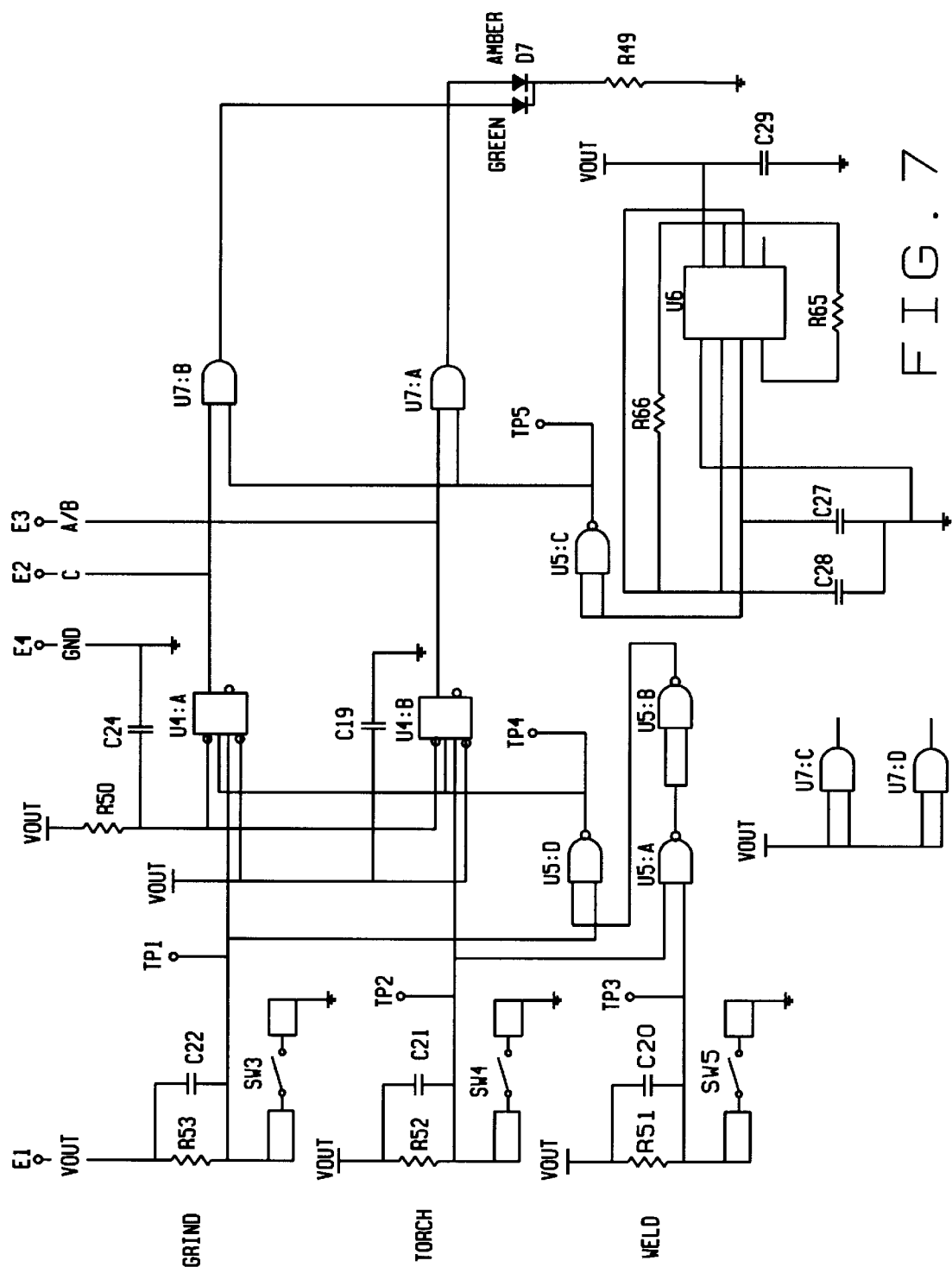
FIG. 7 is a schematic diagram of the electronics comprising the bottom PC board having the fixed shade level controls.

Continuing to refer to FIG. 5, the first fixed shade mode is implemented as follows. U3 knows that the unit is in the "grind" mode from its input that comes from the other PC board as shown in FIG. 7, U3 pins 9, 10, and 11. During the grind mode, U3 pins 15, 2, 3, and 4 will bring the THRES signal (U1 pin 14, 17) up to VOUT, U3 pin 16. The sensor signal U1 pin 15, 18 will not go above VOUT, therefore sensor voltage will not exceed THRES, and the unit will never turn the shutter dark, but will remain clear until the unit times out. It provides the user with a near clear view, yet will not go dark if bright light occurs. The unit will still provide protection to the users eyes, in this mode, from things such as dirt, debris, and infrared and UV electromagnetic energy. Even bright sparks will not turn the shutter dark in this mode.

The second fixed shade mode is implemented as follows. U3 knows that the unit is in the "torch" mode from its input that comes from the other PC board as shown in FIG. 7, U3 pins 9, 10, and 11. During the torch mode, U3 pins 15 and 1 will bring the THRES signal down to ground GND through R54. The sensor signal will always be above ground, as explained above. Therefore the unit will always be dark, until the unit times out. U3 will also short R17, R20 and R48 between pins 13, 14 leaving only R47 and R21 in circuit at a fixed voltage, bringing HVSET to a lower voltage, thus setting the filter to a shade 5. R47 will fine tune the voltage for the shade 5. This mode provides the user with a fixed shade view, which can allow the user to do things such as light torch welding without having to remove the helmet.

Referring now to FIG. 7, this PC board gets its power from the other board through flex cable 68 as connected at terminals E1 and E4. When the unit is powered up, C24 and R50 delay the power to U4's preset inputs (U4 pins 4 and 10). This causes the D-latches preset to be initialized and the output of (Q not), U4 pins 6 and 8, to go low, making the weld mode the default after power up. The board monitors the input from three different pushbuttons (grind, torch, weld). When one of the switches is pressed the D-latch sends a corresponding signal to the other board and will maintain on until a different switch is pressed. The outputs of the D-latches are sent to U3 pins 9, 10 and 11 through the flex cable 68 at terminals E2, E3. When SW3 is pressed a low is sent to the D-latches input and to the same output U4 pin 4. It is then AND'ed with a 70 Hz. signal generated from U6 (555 timer) which turns on and off the LED to save power. The 70 Hz. is fast enough that the user does not see the green LED flicker, while the LED is illuminated. When SW4 is pressed similar to the process explained above, a high is latched into U4 pin 8 (D-latch) and sent to the other board through terminal E3, telling the other board that the user has selected the torch mode. It is also sent to U7 pin 1 and AND'ed with a 70 Hz. signal generated from U6 to save power while powering the amber LED to be illuminated. When SW5 is pressed, both inputs are high (U4 pins 2 and 12), when the CLK goes high from U5. Thus neither D-latches are set and both signals sent to the other board are low (E2 and E3), telling the other board to select the weld mode. No LED is illuminated in the weld mode, making it easy for the welder to distinguish from either fixed mode and the weld mode.

The invention has been disclosed herein in the context of the inventors preferred embodiment. However, changes and modifications thereto as would be apparent to one of ordinary skill in the art is intended to be included by the inventors and the invention should be limited only by the scope of the claims appended hereto, and their equivalents. For example, the particular electronic components chosen by the inventors could be chosen to be different, could be a programmed microprocessor, could be an ASIC, or could be any other electronic logic device so long as it provided the functional logic required. The particular physical arrangement could be changed without departing from the scope and spirit of the invention, as long as the welders vision is not interfered with or obstructed. The particular visual indicators could be chosen as different electronic components, or placed in a different physical location, as long as the welder is given a visual indication that is readily viewable. Still other changes could be envisioned.

What is claimed is:

1. A welding helmet having a shutter assembly, said shutter assembly being capable of adjustment to a plurality of shade levels, a control for automatically adjusting said shutter assembly to a preselected shade level from amongst a plurality of shade levels upon sensing a predetermined light intensity, and an operator input connected to said control for a user to selectively fix and hold at least one preselected shade level for said shutter assembly, said operator selected shade level being suitable for welding.

2. The welding helmet of claim 1 wherein said control fixes and holds said shade level in disregard of any sensed light intensity.

3. The welding helmet of claim 2 wherein said operator input includes an input permitting an operator to selectively fix the shutter assembly in one of a plurality of preselected shade levels.

4. The welding helmet of claim 3 wherein said control is adjustable to permit the shade level of each of said plurality of preselected shade levels to be adjusted.

5. The welding helmet of claim 4 further comprising an indicator for displaying to a user the selection by said user of a preselected shade level.

6. The welding helmet of claim 5 wherein said operator input is accessible inside said helmet and operable as said helmet is worn by a user.

7. The welding helmet of claim 6 wherein said control comprises an electronic circuit mounted on a plurality of circuit boards, and a flexible cable interconnecting said circuit boards to thereby electrically interconnect said electronic circuit.

8. The welding helmet of claim 7 wherein said shutter assembly includes a shutter, at least one of said circuit boards being mounted above said shutter and another of said circuit boards being mounted below said shutter, said flexible cable being routed around said shutter to thereby interconnect said circuit boards.

9. The welding helmet of claim 3 wherein said operator input further comprises a plurality of manually operable buttons, each of said buttons being associated with a preselected shade level so that user operation of a button causes the control to adjust the shade level of said shutter assembly to its associated preselected shade level.

10. The welding helmet of claim 9 wherein said control is responsive to each of said buttons for selecting its associated preselected shade level and not for de-selecting said preselected shade level.

11. The welding helmet of claim 10 further comprising a button for an operator to select said automatic adjustment of said shutter assembly and wherein said control is responsive to each of said buttons, other than said automatic adjustment associated button, for disabling said automatic adjustment upon sensing a predetermined light intensity.

12. The welding helmet of claim 11 wherein said control resets to automatic adjustment, and not to a preselected shade level, upon de-energization of said control.

13. A shutter assembly for a welding helmet, said shutter assembly being capable of adjustment to a plurality of shade levels and comprising a control for automatically adjusting said shutter assembly to a preselected shade level from amongst a plurality of shade levels upon sensing a predetermined light intensity, and an operator input connected to said control for a user to selectively fix and hold at least one preselected shade level for said shutter assembly, said operator selected shade level being suitable for welding.

14. The shutter assembly of claim 13 wherein said control fixes and holds said shade level in disregard of any sensed light intensity.

15. The shutter assembly of claim 14 wherein said operator input includes an input permitting an operator to selectively fix the shutter assembly in one of a plurality of preselected shade levels.

16. The shutter assembly of claim 15 wherein said control is adjustable to permit the shade level of each of said plurality of preselected shade levels to be adjusted.

17. The shutter assembly of claim 16 further comprising an indicator for displaying to a user the selection by said user of a preselected shade level.

18. The shutter assembly of claim 17 wherein said operator input is accessible from inside a helmet within which said shutter assembly is mounted and operable as said helmet is worn by a user.

19. The shutter assembly of claim 18 wherein said control comprises an electronic circuit mounted on a plurality of circuit boards, and a flexible cable interconnecting said circuit boards to thereby electrically interconnect said electronic circuit.

20. The shutter assembly of claim 19 wherein said shutter assembly includes a shutter, at least one of said circuit boards being mounted above said shutter and another of said circuit boards being mounted below said shutter, said flexible cable being routed around said shutter to thereby interconnect said circuit boards.

21. The shutter assembly of claim 15 wherein said operator input further comprises a plurality of manually operable buttons, each of said buttons being associated with a preselected shade level so that user operation of a button causes the control to adjust the shade level of said shutter assembly to its associated preselected shade level.

22. The shutter assembly of claim 9 wherein said control is responsive to each of said buttons for selecting its associated preselected shade level and not for de-selecting said preselected shade level.

23. The shutter assembly of claim 22 further comprising a button for an operator to select said automatic adjustment of said shutter assembly and wherein said control is responsive to each of said buttons, other than said automatic adjustment associated button, for disabling said automatic adjustment upon sensing a predetermined light intensity.

24. The shutter assembly of claim 23 wherein said control resets to automatic adjustment, and not to a preselected shade level, upon de-energization and then re-energization of said control.

25. The shutter assembly of claim 24 further comprising a case for containing said shutter assembly.

26. A welding helmet including a shutter through which a wearer of said helmet may view a welding operation, said shutter having an associated electronic control for controlling a light transmission shade of said shutter, said control including a light sensor for sensing light emanating from said welding operation, said control having an electronic circuit for driving said shutter to a darker shade in response to said light sensor sensing brighter light from said welding operation, and an operator input connected to said control, said control being responsive to said operator input to drive the shutter to a preselected shade associated with said operator input independently of the light emanating from said welding operation.

27. The welding helmet of claim 26 wherein said control disables said light driving electronic circuit upon said operator input being selected.

28. The welding helmet of claim 27 wherein said operator input provides for an operator to select one from a plurality of preselected shades available for said shutter.

29. The welding helmet of claim 28 wherein said operator input further comprises a provision for an operator to select light sensing driving of the shade of said shutter.

30. The welding helmet of claim 29 further comprising a case for containing said shutter and control, and wherein said operator input comprises a plurality of buttons mounted on said case and accessible to an operator from within said helmet.

31. The welding helmet of claim 28 further comprising an illuminated display mounted inside the helmet for indicating to an operator which of said operator selectable shades has been selected.

32. The welding helmet of claim 31 wherein said operator input comprises a plurality of buttons, each of said buttons being associated with a single fixed shade level, except that one button is associated with light sensing adjustment of the shade of said shutter.

33. A method of adjusting the shade of an auto-darkening shutter for a welding helmet comprising:
providing an operator input which when selected by an operator fixes the shade of the shutter to a fixed and associated level, and
disabling the auto-darkening of said shutter upon operator selection of a fixed shade.

34. The method of claim 33 further comprising the step of:
providing an operator input which when selected by an operator activates the auto-darkening portion of said control, and thereby deselects the fixed shade level operator input.

35. A welding helmet includes an electronically controlled, auto-darkening shutter through which a user views his work, and a manual operator input for an operator to select one from amongst a plurality of preselected fixed shade levels for said shutter, said manual operator input being dominant over said auto-darkening feature of said shutter so that once set it is not altered by any incident light.

36. The welding helmet of claim 35 wherein said manual operator input further includes an available operator selection of auto-darkening.

37. The welding helmet of claim 36 wherein said manual operator input comprises a plurality of buttons, each of said buttons having an associated fixed shade level except the button associated with auto-darkening, and wherein each of said buttons when operated deselects the other of said buttons' associated shade levels.

* * * * *